United States Patent [19]

Romine et al.

[11] 4,186,071

[45] Jan. 29, 1980

[54] PROCESS FOR PRODUCING OXYGEN GAS SENSOR ELEMENTS

[75] Inventors: Donald J. Romine; Donald C. Davis, both of Fostoria; Phillip R. Woodruff, Tiffin, all of Ohio; Ching T. Young, Troy, Mich.; James D. Bode, Royal Oak, Mich.; Tseng Y. Tien, Ann Arbor, Mich.

[73] Assignee: Bendix Autolite Corporation, Fostoria, Ohio

[21] Appl. No.: 4,781

[22] Filed: Jan. 19, 1979

Related U.S. Application Data

[63] Continuation-in-part of Ser. No. 885,423, Mar. 13, 1978, Pat. No. 4,136,000.

[51] Int. Cl.$^2$ .................. C23G 1/02; G01N 27/58
[52] U.S. Cl. .................. 204/195 S; 252/472
[58] Field of Search .................. 204/1 S, 195 S; 123/119 E, 119 EC; 60/276; 324/29; 422/98; 252/472

[56] References Cited

U.S. PATENT DOCUMENTS 4,136,000  1/1979  Davis et al. .................. 204/195 S

OTHER PUBLICATIONS

J. E. Bauerle, J. Phys. Chem. Solids, pp. 2657–2670, vol. 30 (1969).

*Primary Examiner*—G. L. Kaplan
*Attorney, Agent, or Firm*—William G. Kratz, Jr.; Raymond J. Eifler

[57] ABSTRACT

An activated oxygen gas sensor element having an increased voltage output under rich gas conditions, short switching response and reduced internal resistance is produced by chemically treating the inner conductive catalyst electrode of the sensor element with an inorganic acid or acid salt and current activating the outer conductive catalyst electrode by applying a direct current to the sensor element, with the outer electrode as a cathode, while the outer electrode is at an elevated temperature and in the presence of a neutral or inert atmosphere. Air may be used as the atmosphere in contact with the outer electrode during the current activation provided that the sensor is subjected to a subsequent reheating step to provide the desired results.

15 Claims, No Drawings

PROCESS FOR PRODUCING OXYGEN GAS SENSOR ELEMENTS

CROSS-REFERENCE TO RELATED APPLICATIONS

This application is a continuation-in-part of an application entitled "Process for Producing Improved Solid Electrolyte Oxygen Gas Sensors" Ser. No. 885,423 filed Mar. 13, 1978 by the present inventors, and now U.S. Pat. No. 4,136,000, the contents of said application being incorporated by reference herein.

BACKGROUND OF THE INVENTION

Oxygen gas sensors are known for use in measuring the oxygen content of an exhaust gas, such as in automobiles, to regulate the efficiency of an engine by varying the air to fuel ratio. One type of such an oxygen gas sensor has a solid electrolyte body in the general shape of a thimble, the solid electrolyte generally comprising a stabilized zirconium dioxide material, with electrodes formed on both the interior and exterior surfaces of the sensor element, the electrodes normally being formed of a catalytic material such as platinum. With the inner electrode exposed to a reference gas such as air, and the outer electrode exposed to the exhaust gas, the oxygen content of the exhaust gas can be measured to determine and regulate the air-fuel ratio of the gas mixture inlet to the engine. The voltage output of such zirconium dioxide sensors normally produce a voltage output the magnitude of which depends upon the oxygen partial pressure in the exhaust gas in which the sensor is immersed. Typically, such sensors, at exhaust temperatures above 350° C., should produce a voltage of about 900 millivolts in an exhaust gas richer than stoichiometry and about 50 millivolts in an exhaust gas leaner than stoichiometry. It has been found, however, that instead of the supposed 900 millivolts to 50 millivolts range, the output ranges of such sensors often would be as low as 0–400 millivolts in the rich gas phase and a negative 200–600 millivolts in the lean phase. The negative voltages occurred most frequently during low exhaust gas temperatures (350° C. or below) and tended to fall into more negative range with increased use.

In addition, the switching time or time required for the sensor to detect a change from rich to lean or lean to rich exhaust gas compositions must be as low as possible, preferably below about a half second (500 milliseconds), again especially during low temperature operation (about 350° C.) such as during engine warm-up.

The internal resistance of the sensor is a further factor which must be controlled since a low internal resistance will allow the sensor to sink or source more useful current from the monitoring system that is being used for determining the oxygen content of the exhaust gas.

The present process provides for the preparation of an oxygen gas sensor element which evidences these improved properties, a high positive voltage output, a fast switching time response and a low internal resistance.

SUMMARY OF THE INVENTION

An oxygen gas sensor element having a high positive voltage output, fast switching response and low internal resistance, the element comprising a solid electrolyte body, such as stabilized zirconium dioxide, and having an inner conductive catalyst electrode on the interior surface thereof for contact with a reference gas and an outer conductive catalyst electrode on the exterior surface thereof for exposure to the exhaust gas, is produced by chemically activating the inner conductive catalyst electrode with an inorganic acid or an acid salt, and subjecting the outer conductive catalyst electrode to a neutral or inert atmosphere, preferably containing moisture, and elevated temperature and applying a direct current to the sensor element under these conditions for a period of time and then maintaining these conditions for a recovery period after cessation of said current. In a further embodiment, the atmosphere to which the outer conductive catalyst electrode is exposed while applying the direct current may be air, provided that the sensor element is susbequently heated to a temperature in excess of about 600° C.

DESCRIPTION OF THE INVENTION

The gas sensor element is in the general shape of a closed tubular member, thimble-like, with the sensor body formed of a solid electrolyte material such as stabilized zirconium dioxide. This general shape of the electrolyte body is known in the art, as well as the solid electrolyte usable. The thimble-like shape of such sensor element, having a shoulder at the open end thereof, is illustrated in U.S. Pat. No. 3,978,006 and other existing publications, which also describe various solid electrolyte materials useful in forming such sensor elements, such as stabilized zirconium dioxide. The preferred composition for forming the solid electrolyte body is a mixture of zirconium dioxide and stabilizing materials such as calcium oxide or yttrium oxide.

To the interior surface of the electrolyte body, an inner electrode of conductive catalyst material is applied, such as by the coating of the surface with a platinum paste with or without a glass frit or other high temperature-resistance bonding material. This paste coating covers the interior surface of the closed terminal end and extends to the shoulder of the electrolyte body. This combination is then fired at a temperature of 600°–1000° C. or higher, as is known in the art, for a sufficient period of time to convert the platinum paste to an electrically conductive inner electrode.

A glass frit or other bonding agent, when used, while providing excellent adherence of the catalytic electrode to the interior surface of the solid electrolyte body, has an effect of increasing the internal electrical resistance of the sensor, and also reducing the positive output voltage of the sensor when the external surface thereof is exposed to a rich atmosphere, and also causing a negative voltage output when the external surface thereof is exposed to a lean atmosphere.

As described in our co-pending parent application, Ser. No. 885,423, the conductive catalyst electrode on the interior surface of the solid electrolyte body is subjected to a chemical activation treatment to improve the voltage output and to reduce the internal resistance of the sensor element. The treatment of the inner conductive catalyst electrode is by contact of the surface thereof with a solution of an inorganic acid or an acid salt. Solutions of an inorganic acid, such as hydrochloric acid, sulfuric acid, nitric acid, phosphoric acid, hydrofluoric acid and chloroplatinic acid are preferred, while acid salts such as ammonium chloride, hydroxylamine hydrochloride, ammonium chloroplatinate or the like, are also usable.

In treating the conductive catalyst electrode with an acidic or acid salt solution, the electrode may be contacted with the solution and the same held in contact for a period of time before removing the solution and rinsing, or the electrode in contact with the solution may be heated to evaporate solvent from the solution and then heated further to elevated temperatures in the range of up to 1200° C.

In addition to the aforedescribed chemical activation of the sensor element inner electrode, the outer electrode is subjected to a current activated treatment.

Both conductive catalyst electrodes, as is known, may comprise platinum or a platinum family-metal catalyst, such as palladium, rhodium or mixtures thereof, with the preferred material being platinum.

In the current activation treatment step of the present invention, the conductive catalyst electrode coating on the exterior surface of the sensor element is subjected to an elevated temperature and a neutral or inert atmosphere, preferably containing moisture, while a direct current is applied to the sensor element with the outer electrode as a cathode and the inner electrode as an anode. Thus, a direct current power source is connected to the conductive catalyst electrode, with the outer electrode connected to the negative terminal and the inner electrode connected to the positive terminal of the power source. After cessation of the current, the sensor element is maintained at the elevated temperature for a period of time for recovery.

In the preferred current activation treatment, the inert or neutral atmosphere in contact with the outer electrode during application of the direct current is nitrogen, although argon or other inert gas may be used, and the atmosphere contains moisture. The term "neutral" or "inert" is used herein to define gases that do not interfere with or chemically react with the sensor components, as well as conventional inert gases. Dry such atmospheres are usable but more beneficial results are obtained where an amount of moisture is included.

In a further embodiment of the current activation treatment, the atmosphere may comprise air but when air is used as the atmosphere in contact with the outer electrode during the application of the direct current, the sensor must be subsequently heated to a temperature of above 600° C., and preferably between 700°–900° C., in order to obtain the desired results.

During the application of the direct current, the conductive catalyst electrode is heated to a temperature in excess of about 500° C. The direct current is applied to the sensor element with the outer electrode as a cathode, the current density being between 5–1000 milliamperes per square centimeter of the planar surface of the outer electrode, for a period of time of about 2–30 minutes. After cessation of the current, the outer electrode is maintained at the elevated temperature for a period of time for recovery.

The current charge usable in the current activation step is one which provides a current density of at least 5 milliamperes per square centimeter of the planar surface of the outer conductive catalyst electrode. The term "current density," as used herein, is determined by dividing the current (in milliamperes) by the planar surface area of the outer conductive catalyst electrode ($cm^2$) on the outer surface of the solid electrolyte body, while the term "planar surface of the outer electrode" is used to define the surface that would be present if the conductive catalyst electrode were a smooth coating without porosity. The preferred range of current density is between 20–150 milliamperes per square centimeter of the outer conductive catalyst electrode surface. Current densities below 5 milliamperes/$cm^2$ are ineffective to give the beneficial results and, while much higher current densities can be used, higher current densities far above the preferred range can cause fracturing of the element through shock. The elevated temperature to which the conductive catalyst coating is exposed is between about 500°–1200° C. with a temperature of between 700°–900° C. being preferred. While at these conditions, a direct current is applied to the sensor element, with the outer electrode as a cathode and the inner electrode as an anode. After cessation of the current, a recovery time of about 3–10 minutes is required, with the conductive catalyst electrode maintained at said elevated temperature.

The following examples further illustrate the present invention. In these examples, the testing of thimbles, as sensor elements, to determine their performance in terms of voltage output under rich and lean conditions, the switching response to gas variation and their internal resistance, was made by inserting the thimbles into protective housings with conductive leads connected to the inner and outer electrode to form sensors. The tests were conducted at 350° C. and at 800° C.

The sensor performance tests were conducted by inserting the sensors into a cylindrical metal tube and exposing them to oxidizing and reducing gaseous atmospheres within the tube through use of a gas burner adjustable to product such atmospheres. Sensors placed in the desired positions in the tube were heated to testing temperature and the voltage output measured using a volt meter. The output was also connected to an oscilloscope to measure the speed of response of the sensor when the burner flame is changed from rich to lean and from lean to rich. A routine test consisted of setting the flame to rich condition, measuring the voltage output of the sensor, switching the flame suddenly to lean condition, triggering the oscilloscope sweep at the same time to record the rich to lean switch of the sensor, switching the flame suddenly back to rich condition, again triggering the oscilloscope to record the sensor output change, and finally adjusting the flame to a lean condition and measuring the sensour output voltage. The switching time is defined as the time period required for the output voltage, as recorded on the oscilloscope, to sweep between 600 and 300 millivolts. When the sensor output voltage under rich gas condition is less than 600 millivolts, the switching response time is not determinable (n/d) according to the criteria used for this switching response measurement. Rich voltage output measurements were then made with different known values of shunting resistance across the sensor terminals. These measurements provided data for calculating the internal resistance of the sensors.

A series of gas sensor electrolyte body thimbles were prepared, for use in the following examples, from ball-milled zirconia, yttria and alumina in a ratio of 80%, 14% and 6% by weight respectively, by isostatically pressing the same in the desired thimble shape and firing at high temperature.

EXAMPLE I

Ten of the series of electrolyte body thimbles, (A32-5, A32-7, A31-10, A32-16, A32-3, A32-9, A34-5, A34-6, A34-1 and A34-3) had an inner electrode applied to the inner surface thereof by coating the inner surface with a platinum suspension containing a glass frit for bonding purposes. The thimble with its inner electrode was then heated in an oxidizing atmosphere to burn off the organic constituents of the suspension and bond the platinum to the zirconia surface. The external platinum catalyst electrode was next applied to the outer surface of the thimble by known thermal vapor deposition. A porous ceramic coating was applied over the external catalyst layer for protection.

Two of the thimbles (A32-5 and A32-7) were then set aside and tested later with the chemically and current activated thimbles, the results of the tests of these two thimbles being listed in Table I as "Control."

The remaining eight thimbles were subjected to chemical treatment by applying to the inner surface thereof a methanol solution of two normal chloroplatinic acid by filling the interior portion of the thimbles with the acid. The filled sensors were then heated to 60° C. for a one hour period, followed by a ten minute period of 800° C. to drive off the volatiles.

These eight thimbles were then subjected to a current activation by inserting the thimbles, as sensors in a protective housing and with conductive leads, into a manifold, with the outer surface of the sensor elements thereof having the outer conductive catalyst coating thereon exposed, while preheated during a ten minute period to a temperature of 750° C., in a flow of 0.5% CO in nitrogen or a flow of 0.5% $H_2$ in nitrogen (with 0.003 mg/cm$^3$ water vapor where indicated as "wet") as indicated in Table I, at a flow rate of 710 cm$^3$/min. The inner conductive catalyst electrode was in contact with air, and the temperature of the sensor was taken at the bottom of the inner region of the sensor element. The sensors were then subjected to a direct current, with the outer electrode as a cathode, for a ten minute period, the direct current charge applied at a current density of 100 milliamperes/cm$^2$ of the outer electrode planar surface, with the gas flow continued. The direct current was then stopped and the sensor elements allowed a recovery period of ten minutes at said temperature and with the outer electrode in said gas flow.

The ten sensors were then tested at 800° C. followed by testing at 350° C. to determine voltage output, switching response and internal resistance. The results of these tests are listed in Table I.

TABLE I

| | | 350° Testing | | | | |
| | | Voltage Output | | Switching Response | | Internal Resistance |
| Sensor | Gaseous Atmosphere | Rich (mv) | Lean (mv) | RL (ms) | LR (ms) | tance (kΩ) |
|---|---|---|---|---|---|---|
| A32-5 | Control | 216 | −436 | n/d | n/d | 850 |
| A32-7 | Control | 252 | −357 | n/d | n/d | 829 |
| A31-10 | $N_2$ (wet CO) | 902 | −18 | 50 | 45 | 12 |
| A32-16 | $N_2$ (wet CO) | 971 | 49 | 70 | 40 | 10 |
| A32-3 | $N_2$ (dry CO) | 634 | −13 | 260 | 660 | 267 |
| A32-9 | $N_2$ (dry CO) | 626 | 39 | 280 | 660 | 273 |
| A34-5 | $N_2$ (wet $H_2$) | 937 | 36 | 60 | 50 | 21 |
| A34-6 | $N_2$ (wet $H_2$) | 887 | −22 | 60 | 55 | 7 |
| A34-1 | $N_2$ (dry $H_2$) | 938 | 36 | 70 | 60 | 28 |

TABLE I-continued

| A34-3 | $N_2$ (dry $H_2$) | 896 | 6 | 60 | 70 | 31 |
|---|---|---|---|---|---|---|
| | | 800° Testing | | | | |
| | | Voltage Output | | Switching Response | | Internal Resistance |
| Sensor | Gaseous Atmosphere | Rich (mv) | Lean (mv) | RL (ms) | LR (ms) | tance (Ω) |
| A32-5 | Control | 820 | 53 | 25 | 70 | 583 |
| A32-7 | Control | 816 | 37 | 25 | 80 | 275 |
| A31-10 | $N_2$ (wet CO) | 814 | 82 | 25 | 30 | 10 |
| A32-16 | $N_2$ (wet CO) | 804 | 78 | 35 | 40 | 9 |
| A32-3 | $N_2$ (dry CO) | 825 | 96 | 45 | 45 | 15 |
| A32-9 | $N_2$ (dry CO) | 828 | 99 | 45 | 70 | 16 |
| A34-5 | $N_2$ (wet $H_2$) | 804 | 81 | 35 | 40 | 11 |
| A34-6 | $N_2$ (wet $H_2$) | 807 | 76 | 35 | 45 | 9 |
| A34-1 | $N_2$ (dry $H_2$) | 800 | 74 | 30 | 35 | 8 |
| A34-3 | $N_2$ (dry $H_2$) | 814 | 92 | 30 | 25 | 9 |

As illustrated in Table I, the sensors that are subjected to the process of the present invention show significantly improved properties relative to the control sensors, especially at 350° C. The voltage output is increased, internal resistance lowered and switching time response improved. Also, the presence of moisture is beneficial.

EXAMPLE II

Six other thimbles of the series of electrolyte thimbles (A35-1, A35-2, A35-3, A35-4, A35-5 and A35-6) had inner and outer electrodes applied thereto as such application was effected in Example I. These six sensor elements were then subjected to chemical treatment in accordance with the chemical treatment described in Example I and were subsequently tested as to voltage output, switching response and internal resistance. The results of the tests are listed in Table II under the designation "Before Activation." These six sensor elements were then subjected to current activation by insertion into a manifold with the outer conductive catalyst coating exposed to a flow of 710 cm$^3$/min. of nitrogen gas containing an amount of water (ppm) as indicated in Table II, while the elements were heated to 750° C. during a ten minute period. At a temperature of 750° C., and with the outer electrode subjected to the nitrogen atmosphere containing the moisture indicated, the sensor elements had applied thereto a direct current, with the outer electrode as a cathode, for a ten minute period, the direct current charge applied at a current density of 100 milliamperes/cm$^2$ of the outer electrode planar surface, while the gas flow was continued. The direct current was then stopped and the sensor element allowed a recovery period of ten minutes at said temperature and with the outer electrode in the indicated gas flow.

These six sensors were then again tested as to voltage output, switching response and internal resistance at 800° C. and 350° C. The results of these tests are listed in Table II under the designation "After Current Activation."

TABLE II

| | | 350° Testing | | | | | 800° Testing | | | | |
| | | Voltage Output | | Switching Response | | Internal Resistance | Voltage Output | | Switching Response | | Internal Resistance |
| Sensor | Treatment | Rich (mv) | Lean (mv) | RL (ms) | LR (ms) | tance (kΩ) | Rich (mv) | Lean (mv) | RL (ms) | LR (ms) | tance (Ω) |
|---|---|---|---|---|---|---|---|---|---|---|---|
| | Before Activation | | | | | | | | | | |
| A35-1 | — | 947 | 176 | 4600 | 55 | 16 | 768 | 66 | 15 | 40 | 29 |
| A35-2 | — | 925 | 139 | 4300 | 55 | 18 | 774 | 68 | 15 | 40 | 30 |

TABLE II-continued

| | | 350° Testing | | | | | 800° Testing | | | | |
|---|---|---|---|---|---|---|---|---|---|---|---|
| | | Voltge Output | | Switching Response | | Internal Resistance | Voltage Output | | Switching Response | | Internal Resistance |
| Sensor | Treatment | Rich (mv) | Lean (mv) | RL (ms) | LR (ms) | tance (kΩ) | Rich (mv) | Lean (mv) | RL (ms) | LR (ms) | tance (Ω) |
| A35-3 | — | 912 | 151 | 5450 | 60 | 30 | 765 | 66 | 20 | 65 | 28 |
| A35-4 | — | 845 | 104 | 2300 | 90 | 63 | 777 | 70 | 15 | 50 | 35 |
| A35-5 | — | 894 | 144 | 4400 | 75 | 37 | 789 | 67 | 15 | 55 | 41 |
| A35-6 | — | 917 | 128 | 3200 | 65 | 26 | 785 | 64 | 20 | 55 | 35 |
| | After Current Activation | | | | | | | | | | |
| | Nitrogen Atmosphere ($H_2O$ Content-ppm) | | | | | | | | | | |
| A35-1 | 170 | 881 | 37 | 165 | 140 | 88 | 792 | 74 | 30 | 40 | 15 |
| A35-2 | 170 | 870 | 36 | 195 | 170 | 87 | 814 | 73 | 25 | 35 | 15 |
| A35-3 | 1100 | 888 | 23 | 130 | 110 | 70 | 812 | 70 | 30 | 25 | 15 |
| A35-4 | 1100 | 879 | 23 | 150 | 130 | 92 | 817 | 68 | 35 | 45 | 30 |
| A35-5 | 2150 | 934 | 29 | 75 | 65 | 32 | 813 | 66 | 25 | 30 | 20 |
| A35-6 | 2150 | 932 | 19 | 65 | 55 | 26 | 812 | 73 | 25 | 20 | 11 |

The beneficial effect of a moisture content is shown by the results listed in Table II, where it is shown that although dry nitrogen is effective as the gaseous atmosphere to which the outer electrode is subjected (only 170 ppm moisture), more beneficial results are obtained where moisture is present.

EXAMPLE III

In this example, the effect of a reheating step on a current activated sensor element which is current activated in the presence of a neutral or inert gas (nitrogen) is illustrated, where the element is tested at 350° C. after current activation, reheated to 800° C. for testing at that temperature and then tested again at 350° C. to illustrate the change in properties thereof.

Four additional thimbles of the series of electrolyte thimbles (A36-82, A36-83, A32-26 and A32-28) had inner and outer electrodes applied and were chemically treated as described in Example I. The four sensors were then subjected to current activation by insertion into a manifold with the outer conductive catalyst coating exposed to a flow of nitrogen gas (710 cm³/min.). The nitrogen gas in contact with the outer electrodes of A36-82 and A36-83 contained 0.003 mg/cm³ of water vapor, "wet," using a current density of 100 milliamperes/cm² of the outer electrode planar surface, with the gas flow continued. The thimbles were preheated to 750° C. during ten minutes, and the direct current applied, with the outer electrode as cathode, for a period of ten minutes at that temperature. After cessation of the current, the sensor elements were allowed a recovery period of ten minutes at said temperature and with the outer electrode exposed to the gas flow.

The sensors were then tested as to voltage output, switching response and internal resistance at 350° C., "First 350° Testing." The sensors were then heated to 800° C. and tested. After the heating to 800° C. testing, the sensors were subsequently again tested at 350° C. "Second 350° Testing." The results of the tests and effect of the reheating of the sensors to a high temperature are illustrated in Table III.

TABLE III

| | | First 350° Testing | | | | |
|---|---|---|---|---|---|---|
| | | Voltage Output | | Switching Response | | Internal Resistance |
| Sensor | Gaseous Atmosphere | Rich (mv) | Lean (mv) | RL (ms) | LR (ms) | tance (kΩ) |
| A36-82 | $N_2$ (wet) | 901 | 7 | 160 | 140 | 48 |
| A36-83 | $N_2$ (wet) | 919 | 70 | 190 | 150 | 74 |
| A32-26 | $N_2$ (dry) | 916 | 240 | >1500 | 200 | 93 |
| A32-26 | $N_2$ (dry) | 720 | 271 | >2000 | 700 | 250 |
| | | 800° Testing | | | | |
| | | Voltge Output | | Switching Response | | Internal Resistance |
| Sensor | Gaseous Atmosphere | Rich (mv) | Lean (mv) | RL (ms) | LR (ms) | tance (Ω) |
| A36-82 | $N_2$ (wet) | 834 | 93 | 40 | 55 | 23 |
| A36-83 | $N_2$ (wet) | 837 | 91 | 30 | 35 | 21 |
| A32-26 | $N_2$ (dry) | 802 | 75 | 30 | 40 | 10 |
| A32-28 | $N_2$ (dry) | 820 | 83 | 40 | 40 | 11 |
| | | Second 350° Testing | | | | |
| | | Voltage Output | | Switching Response | | Internal Resistance |
| Sensor | Gaseous Atmosphere | Rich (mv) | Lean (mv) | RL (ms) | LR (ms) | tance (kΩ) |
| A36-82 | $N_2$ (wet) | 884 | 10 | 180 | 180 | 101 |
| A36-83 | $N_2$ (wet) | 914 | 58 | 190 | 130 | 75 |
| A32-26 | $N_2$ (dry) | 845 | 49 | 150 | 160 | 52 |
| A32-28 | $N_2$ (dry) | 899 | 142 | 350 | 200 | 77 |

As shown by the results listed in Table III, where wet nitrogen is used as the atmosphere to which the outer coating is exposed, the sensor performs well at 350° C., whereas the use of dry nitrogen gives less satisfactory results. After reheating the sensors that were activated in the presence of dry nitrogen, however, to 800° C. during the subsequent test, the properties of even these sensors are much improved. Thus, the reheating of the sensor element following activation improves the properties thereof.

EXAMPLE IV

A further embodiment of the process of the present invention is illustrated herein, where the outer electrode of the thimble is exposed to air during current activation. Four additional thimbles of the series of electrolyte thimbles (A36-90, A36-91, A36-92 and A36-93) had inner and outer electrodes applied and were chemically treated as described in Example I. The four sensors were then subjected to current activation by insertion into a manifold with the outer conductive catalyst coating exposed to a flow of air (710 cm³/min.). The air in contact with the outer electrodes of A36-90 and A36-91 contained 0.003 mg/cm³ of water vapor, "wet," with a direct current applied at a current density of 100 milliamperes/cm² of the outer electrode planar surface, the flow of air being continued. A preheating time of ten minutes was used to heat the thimbles to 750° C. and the direct current applied for a period of ten minutes at that temperature with the outer electrode as a cathode. After cessation of the current, the element was allowed a recovery period of ten minutes at 750° C. while the air flow continued.

The sensors were tested for voltage output, switching response and internal resistance at 350° C., "First 350° Testing." The sensors were then tested at 800° C. After this high temperature treatment, the sensors were again tested at 350° C. "Second 350° Testing." The results of the three series of tests are illustrated in Table IV.

TABLE IV

| | | First 350° Testing | | | | |
|---|---|---|---|---|---|---|
| | | Voltage Output | | Switching Response | | Internal Resistance |
| Sensor | Gaseous Atmosphere | Rich (mv) | Lean (mv) | RL (ms) | LR (ms) | tance (kΩ) |
| A36-90 | Air (wet) | 947 | 129 | 1800 | 210 | 32 |
| A36-91 | Air (wet) | 945 | 74 | 600 | 140 | 19 |
| A36-92 | Air (dry) | 978 | 136 | 1000 | 130 | 35 |
| A36-93 | Air (dry) | 974 | 125 | 950 | 130 | 31 |

| | | 800° Testing | | | | |
|---|---|---|---|---|---|---|
| | | Voltage Output | | Switching Response | | Internal Resistance |
| Sensor | Gaseous Atmosphere | Rich (mv) | Lean (mv) | RL (ms) | LR (ms) | tance (Ω) |
| A36-90 | Air (wet) | 818 | 84 | 45 | 80 | 15 |
| A36-91 | Air (wet) | 815 | 87 | 35 | 60 | 14 |
| A36-92 | Air (dry) | 823 | 82 | 55 | 90 | 18 |
| A36-93 | Air (dry) | 825 | 84 | 45 | 75 | 15 |

| | | Second 350° Testing | | | | |
|---|---|---|---|---|---|---|
| | | Voltge Output | | Switching Response | | Internal Resistance |
| Sensor | Gaseous Atmosphere | Rich (mv) | Lean (mv) | RL (ms) | LR (ms) | tance (kΩ) |
| A36-90 | Air (wet) | 952 | 65 | 270 | 120 | 15 |
| A36-91 | Air (wet) | 939 | 39 | 140 | 130 | 33 |
| A36-92 | Air (dry) | 942 | 48 | 200 | 110 | 33 |
| A36-93 | Air (dry) | 943 | 53 | 190 | 130 | 48 |

Thus, although it was initially believed that the use of air as the atmosphere in contact with the outer electrode during current activation was ineffective, and such as is still believed to be ineffective, by reheating such treated sensor elements to a temperature of between 700°–900° C., preferably about 800° C., the sensor elements do achieve improved performance over untreated such elements.

What is claimed is:

1. A process for producing an activated oxygen gas sensor element having an increased voltage output under rich gas conditions, shortened switching response time and reduced internal resistance, wherein the sensor element comprises a solid electrolyte body having an inner conductive catalyst electrode on the inner surface and an outer conductive catalyst electrode on the outer surface thereof, comprising:
   (a) contacting said inner conductive catalyst electrode with an acidic reactant selected from the group consisting of inorganic acids and acid salts;
   (b) applying a direct current to the sensor element, with said outer conductive catalyst electrode as a cathode, while subjecting said outer conductive catalyst electrode to a neutral or inert atmosphere at an elevated temperature in excess of 500° C., the current density thereof being at least 5 milliamperes per square centimeter of the planar surface of said outer conductive catalyst electrode; and
   (c) maintaining said outer electrode, after cessation of said current, at the elevated temperature for a period of time for recovery.

2. The process for producing an activated oxygen gas sensor element as defined in claim 1 wherein said atmosphere contains moisture.

3. The process for producing an activated oxygen gas sensor element as defined in claim 1 wherein said atmosphere consists essentially of nitrogen.

4. The process for producing an activated oxygen gas sensor element as defined in claim 1 wherein said contacting of the inner electrode with said acidic reactant is effected and thereafter the application of said direct current to the outer electrode is effected.

5. The process for producing an activated oxygen gas sensor element as defined in claim 1 wherein said application of the direct current to the outer electrode is effected and thereafter said contacting of the inner electrode with said acidic reactant is effected.

6. The process for producing an activated oxygen gas sensor element as defined in claim 1 wherein said direct current is applied while the sensor element is at an elevated temperature of between 500°–1200° C.

7. The process for producing an activated oxygen gas sensor element as defined in claim 1 wherein said direct current is applied at a current density of between 5–1000 milliamperes per square centimeter of the planar surface of said outer electrode.

8. The process for producing an activated oxygen gas sensor element as defined in claim 1 wherein said direct current is applied for a period of time of between 2–30 minutes.

9. The process for producing an activated oxygen gas sensor element as defined in claim 1 wherein said period of time for recovery is in excess of 3 minutes.

10. The activated oxygen gas sensor element produced according to the process of claim 1.

11. A process for producing an activated oxygen gas sensor element having an increased voltage output under rich gas conditions, shortened switching response time and reduced internal resistance, wherein the sensor element comprises a zirconium dioxide body having an inner platinum electrode on the inner surface and an outer platinum electrode on the outer surface thereof, comprising:
   (a) contacting said inner platinum electrode with an acidic reactant selected from the group consisting of inorganic acids and acid salts;
   (b) applying a direct current to the sensor element, with said outer platinum electrode as a cathode, while subjecting said outer platinum electrode to a moisture-containing nitrogen atmosphere at an elevated temperature between 600°–900° C., the current density thereof being between 20–150 milliamperes per square centimeter of the planar surface of said outer platinum electrode; and
   (c) maintaining said outer electrode, after cessation of said current, at the elevated temperature for a period of time for recovery.

12. A process for producing an activated oxygen gas sensor element having an increased voltage output under rich gas conditions, shortened switching response time and reduced internal resistance, wherein the sensor element comprises a solid electrolyte body having an inner conductive catalyst electrode on the inner surface and an outer conductive catalyst electrode on the outer surface thereof, comprising:

(a) contacting said inner conductive catalyst electrode with an acidic reactant selected from the group consisting of inorganic acids and acid salts;

(b) applying a direct current to the sensor element, with said outer conductive catalyst electrode as a cathode, while subjecting said outer conductive catalyst electrode to an elevated temperature in excess of 500° C., in the presence of air, the current density of said direct current being at least 5 milliamperes per square centimeter of the planar surface of said outer conductive catalyst electrode;

(c) maintaining said outer electrode, after cessation of said current, at said elevated temperature for a period of time for recovery; and (d) subsequently reheating said sensor element to a temperature in the range of 700°–900° C.

13. The process for producing an activated oxygen gas sensor element as defined in claim 12 wherein said electrodes comprise platinum.

14. The process for producing an activated oxygen gas sensor element as defined in claim 12 wherein said air contains moisture.

15. The activated oxygen gas sensor produced according to the process of claim 12.

* * * * *